(12) United States Patent
Herbst et al.

(10) Patent No.: US 7,078,709 B2
(45) Date of Patent: Jul. 18, 2006

(54) APPARATUS AND METHOD FOR PROOF OF OUTGASSING PRODUCTS

(75) Inventors: Waltraud Herbst, Uttenreuth (DE); Karl Kragler, Erlangen (DE); Michael Sebald, Weisendorf (DE)

(73) Assignee: Infineon Technologies AG, Munich (DE)

( * ) Notice: Subject to any disclaimer, the term of this patent is extended or adjusted under 35 U.S.C. 154(b) by 0 days.

(21) Appl. No.: 10/974,829

(22) Filed: Oct. 28, 2004

(65) Prior Publication Data

US 2005/0092936 A1    May 5, 2005

(30) Foreign Application Priority Data

Oct. 30, 2003    (DE) .............................. 103 50 688

(51) Int. Cl.
*A61N 5/00*    (2006.01)

(52) U.S. Cl. .............................. 250/492.2; 250/458.1; 250/461.1; 355/53; 355/72; 438/16

(58) Field of Classification Search ............... None
See application file for complete search history.

(56) References Cited

U.S. PATENT DOCUMENTS

| | | | |
|---|---|---|---|
| 6,369,887 B1 | 4/2002 | Eyolfson et al. | |
| 6,555,825 B1 * | 4/2003 | Mitchell et al. | 250/398 |
| 2002/0030801 A1 * | 3/2002 | Endo et al. | 355/53 |
| 2005/0079438 A1 * | 4/2005 | Cao et al. | 430/270.1 |

* cited by examiner

*Primary Examiner*—Nikita Wells
*Assistant Examiner*—Zia R. Hashmi
(74) *Attorney, Agent, or Firm*—Edell Shapiro & Finnan, LLC

(57) ABSTRACT

Outgassing products, which are formed during the exposure of photoresist systems by laser irradiation, are adsorbed on a proof plate for further analysis.

18 Claims, 2 Drawing Sheets

US 7,078,709 B2

APPARATUS AND METHOD FOR PROOF OF OUTGASSING PRODUCTS

CROSS REFERENCE TO RELATED APPLICATIONS

This application claims priority under 35 USC §119 to German Application No. DE 103 50 688.8, filed on Oct. 30, 2003, and titled "Apparatus and Method for Proof of Outgassing Products," the entire contents of which are hereby incorporated by reference.

FIELD OF THE INVENTION

The invention relates to an apparatus and a method for proof of outgassing products which are produced during the exposure of photoresists.

BACKGROUND

Microchips are produced in a large number of process steps, in which changes are deliberately made within a small section of the surface of a substrate, i.e., a silicon wafer, in order, for example, to introduce trenches for deep-trench capacitors into the substrate, or to deposit thin interconnects or electrodes on the substrate surface.

To display such small structures, a mask is produced on the substrate surface so that those areas which are intended to be processed are exposed, while other areas are protected by the mask. After processing, the mask is removed from the substrate surface, for example, by incineration.

The mask is produced by applying a thin layer of a photoresist, which has a film-forming polymer as well as a photosensitive compound. This film is subsequently exposed with a mask, for example, being introduced into the beam path, which has information about the structure to be produced and which is used for selective exposure of the photoresist film. For production purposes, the mask is projected onto the photoresist film via a high-resolution lens system.

Photoresist systems are currently subject to rapid technical developments and have major financial importance. The exposure for structuring of photoresists in this case requires complex and expensive beam optics.

Difficulties can occur when radiation at a short wavelength is used to expose the photoresist. An exposure wavelength of 248 nm, and particularly at even shorter wavelengths, the high energy of the illumination radiation breaks bonds in the polymer. For example, the photon energy of 7.9 eV at 157 nm is above typical bonding energies of resist polymers, and the photon energy in the EUV band (extreme ultraviolet) with wavelengths around 13 nm is, for example, 95 eV. Polymer systems for exposure wavelengths of 248 nm and below release gaseous decomposition products, which have silicon or other decomposition products, which are damaging to the lens systems.

These decomposition products, which have silicon, can relatively slowly be converted by the residual oxygen present in the flushing gas into silicon dioxide, which can be precipitated onto the exposure optics and can "blind" them over the course of time.

Damage and contamination of the lens systems resulting from decomposition products adversely effect the optical characteristics, and thus the quality of the mask structure that is formed. This contamination may even lead to irreversible damage to the lenses. This results in replacement costs to the damaged optical systems, and maintenance costs caused by production failure.

To be able to investigate the behavior of photoresist systems during exposure and the formation of outgassing products is necessary. The corresponding investigation results may then provide opportunities to carry out chemical adaptation to the photoresist or to institute apparatus measures for protection of the lens systems.

Since the rate of development in photoresist technology is high and is increasing further, it is necessary to obtain appropriate information about the outgassing behavior of the photoresist quickly and reliably.

The connections, which are precipitated on the front lenses during the outgassing process and change their optical characteristics, are of particular interest.

It is known to irradiate photoresist systems with an electron beam in a vacuum and to gather the outgassing products by a refrigerated trap. The frozen-out materials are then vaporized separately and can be analyzed by mass spectrometry.

However, with this method, only an incomplete picture of the compounds, which are produced during the exposure process, is obtained due to the short life of some compounds or possible subsequent rearrangement or decomposition processes. Furthermore, electron bombardment cannot be transferred to exposure with photons in an unrestricted manner. Also, a large amount of time is required for this method.

Furthermore, the substances, which are released in comparable methods, are specified based on their detectability by the appropriate proof methods (gas chromatography or mass spectrometry) and their adsorption behavior on optical lenses is not detected.

The critical factor is to record the characteristic of these compounds to become fixed reversibly or irreversibly on a lens surface, and to adversely affect the optical characteristics of such a lens surface. This feature is not detected by the conventional methods and apparatuses.

An apparatus which allows the photoresist system outgassing products which are produced during exposure and are adsorbed reversibly or irreversibly on the lens surfaces to be investigated, is desirable.

Also, to preselect resist systems which are suitable for further industrial use based on emitting relatively small amounts of hazardous outgassing products, is desirable.

SUMMARY

An apparatus for proof of outgassing products can include a radiation source for emission of radiation, beamforming optics, a substrate holder which can be rotated and moved, and a proof plate for adsorption of the outgassing products which are emitted from a substrate.

The radiation source, for example, an excimer laser, produces the radiation energy required for exposing the photoresist. The resolution of the mask structure to be produced can be varied in a suitable form by selection of an appropriate wavelength. In particular, wavelengths of 248 nm, 193 nm and 157 nm are relevant to the field of microelectronics.

The beamforming optics are used to focus the radiation by suitable lens systems, and to align it with the desired irradiation area. Furthermore, the exposure intensity can be adjusted in a manner by, for example, widening or narrowing the beam path.

The radiation strikes a substrate and produces the intended exposure effect.

A proof plate is provided between the beamforming optics and the substrate and simulates the front lens of an exposure appliance, on which the outgassing products which are released by the radiation energy can be precipitated in the form of reversible or irreversible adsorption. The substances, which adhere to the proof plate, may then be detected by appropriate chemical or physical proof methods. Surface-analytical methods, such as XPS (X-ray photoelectron spectroscopy), are, for example, particularly suitable for this purpose. In this method, high-energy X-rays are used to release photoelectrons from the inner shells of the elements to be proven, and their energy is detected in an appropriate form. The initial energy of a photoelectron released from an atom can be calculated from the known energy of the X-ray radiation provided. This initial energy is characteristic of each element and thus allows the elements in the surface composition to be analyzed.

In order to record the incident radiation energy during irradiation, and thus to link open-loop and/or closed-loop control processes, a detector can be provided on the plane of the substrate. The detector can be moved into the beam path before the exposure and can measure radiation energy striking the substrate to record the exposure sequence. The dose measurement system may also be installed in the beam guidance via beam splitters. Dosage monitoring during exposure is thus possible.

In one embodiment of the invention, the substrate is a photoresist. The photoresist can be a chemically enhanced photoresist. Chemically enhanced photoresists have photolabile photoacids, which can release decomposition products when exposed and which may be damaging to the apparatus environment. In particular, acidic products, which are released, may attack and damage the glass materials of lenses. Materials having fluorine, for example, have no resistance to acids, and are easily attacked. In this case, for instance, fluorinated quartz, calcium fluoride, and magnesium fluoride are frequently used as glass materials, with the fluoride anions being removed from the crystal when attacked by acid, and thus destroying the lattice structure.

In the case of photoresist systems, which are retrospectively enhanced chemically by organosilicon compounds, silicon salts, which are resistive and are difficult to remove and may severely adversely affect the optical quality of the lenses, are produced, particularly on the lens systems.

The photoresist can be applied to a wafer. This arrangement also corresponds to the real constellation, so that the outgassing characteristics of the photoresist can be investigated in realistic conditions.

In one embodiment of the invention, the radiation is at a wavelength, for example, below 200 nm. The resolution of the mask structure to be produced and thus the size of the microelectronic components to be formed are scaled with the wavelength of the radiation used. The integration density of the present-day generation of electronic components requires a wavelength, which is, at most, not more than 200 nm. Future generations may relatively more stringent requirements.

As the wavelength increases, the amount of energy transported by the photons rises. The higher this energy, the greater the probability of bonds within the polymer that is used in the photoresist being broken. Even a wavelength of 157 nm with a photon energy of 7.9 eV results in an amount of energy, which is greater than the bonding energy of conventional resist polymers. The photon energy of 95 eV in the EUV (extreme ultraviolet) band, which is becoming increasingly important, is relatively higher, and can cause more inadvertent bonding breakdowns in the resist.

The proof plate is, for example, fixed by a holder. The holder allows accurate adjustment of the proof plate in the immediate vicinity of the photoresist. The non-variable position also ensures that the experimental conditions are always the same, and ensures the validity of the results obtained.

In one embodiment of the invention, a nitrogen flow flows around the proof plate. The nitrogen flow ensures that contamination of the substrates by molecules from the surrounding air, and a consequent negative influence on the measurement, are avoided.

In one embodiment of the invention, the nitrogen flow flows around the proof plate in an annular shape. The symmetrically produced flow profiles result in local homogeneity of the concentration and temperature distribution, and uniform environmental conditions. The irradiation process thus produces reproducible and valid results. At the same time, the introduction of environmental oxygen, which oxidizes compounds to be proven and other contaminants, is reduced to a minimum.

The flow rate of the nitrogen flow is variable, and is matched to the experimental requirements. If the flow rate is too slow, reliable screening of the environmental air is not ensured and contamination is possible, while an excessively strong nitrogen flow results in there being a risk of outgassing products diffusing out of the substrate surface being torn away by the nitrogen flow, and no longer reaching the proof plate, for detection.

In order for the molecules which leave the photoresist to be precipitated on the proof plate, this proof plate can be arranged a short distance in front of the substrate. The shorter the distance between the proof plate and the substrate surface, the greater is the proportion of outgassing molecules, which are adsorbed on the proof plate.

The surface concentration of these compounds on the plate thus rises, thus improving the accuracy of the subsequent physical/chemical analysis.

For example, the distance can be 0.3 mm.

The substrate can be fixed on a substrate holder. The substrate holder allows accurate adjustment of the substrate in the immediate vicinity of the proof plate. The non-variable position also guarantees that the experimental conditions are always the same, thus improving the validity of the results obtained.

The substrate holder can, for example, be rotatable and/or movable. This allows the exposure area on the substrate to be varied easily. Furthermore, the capability to vary the distance between the substrate and the proof plate makes it possible to determine and study the influence of this distance on the concentration of the outgassing products, for example, by production of a concentration profile. This opens up the possibility, taking account of the optical conditions, to deduce the optimum distance between the substrate and the front lens.

The apparatus according to the invention can be used in a method for proof of outgassing products.

BRIEF DESCRIPTION OF THE DRAWINGS

The invention will be explained in more detail using an exemplary embodiment and with reference to the attached figures, in which, in detail.

DETAILED DESCRIPTION

Figure 1:
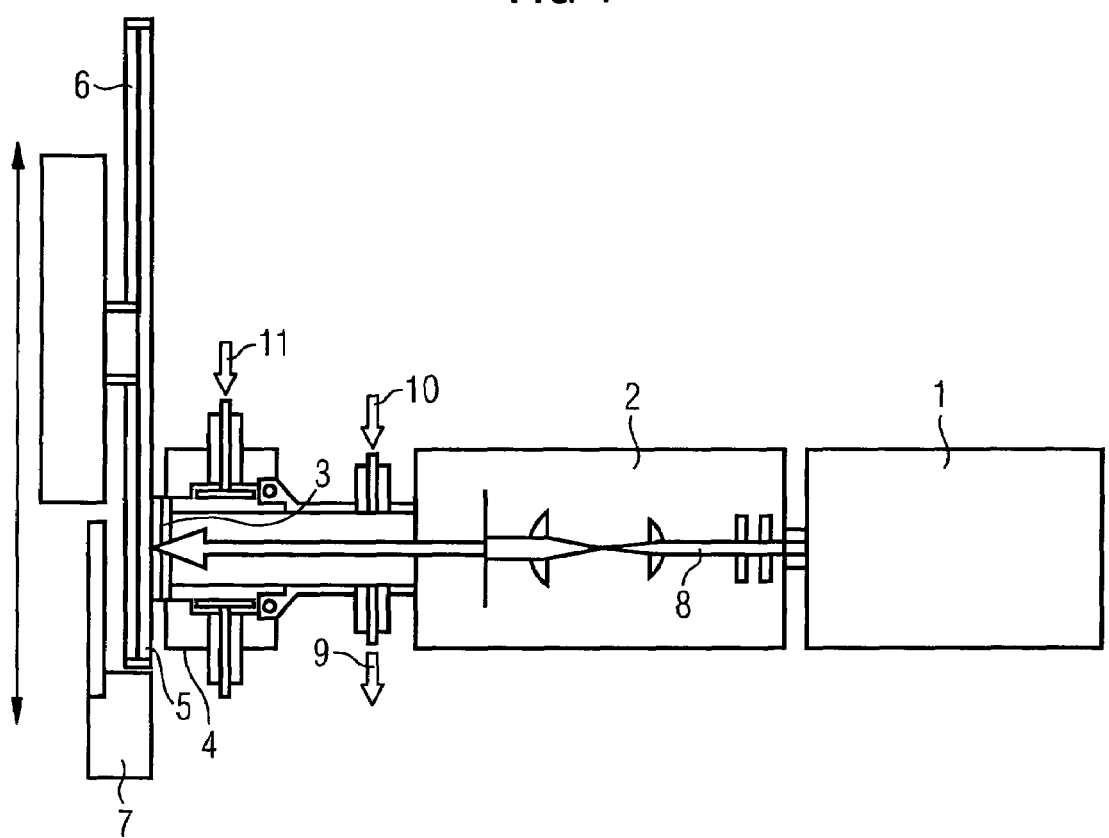
FIG. 1 shows the schematic layout of the apparatus according to the invention.
Figure 2:
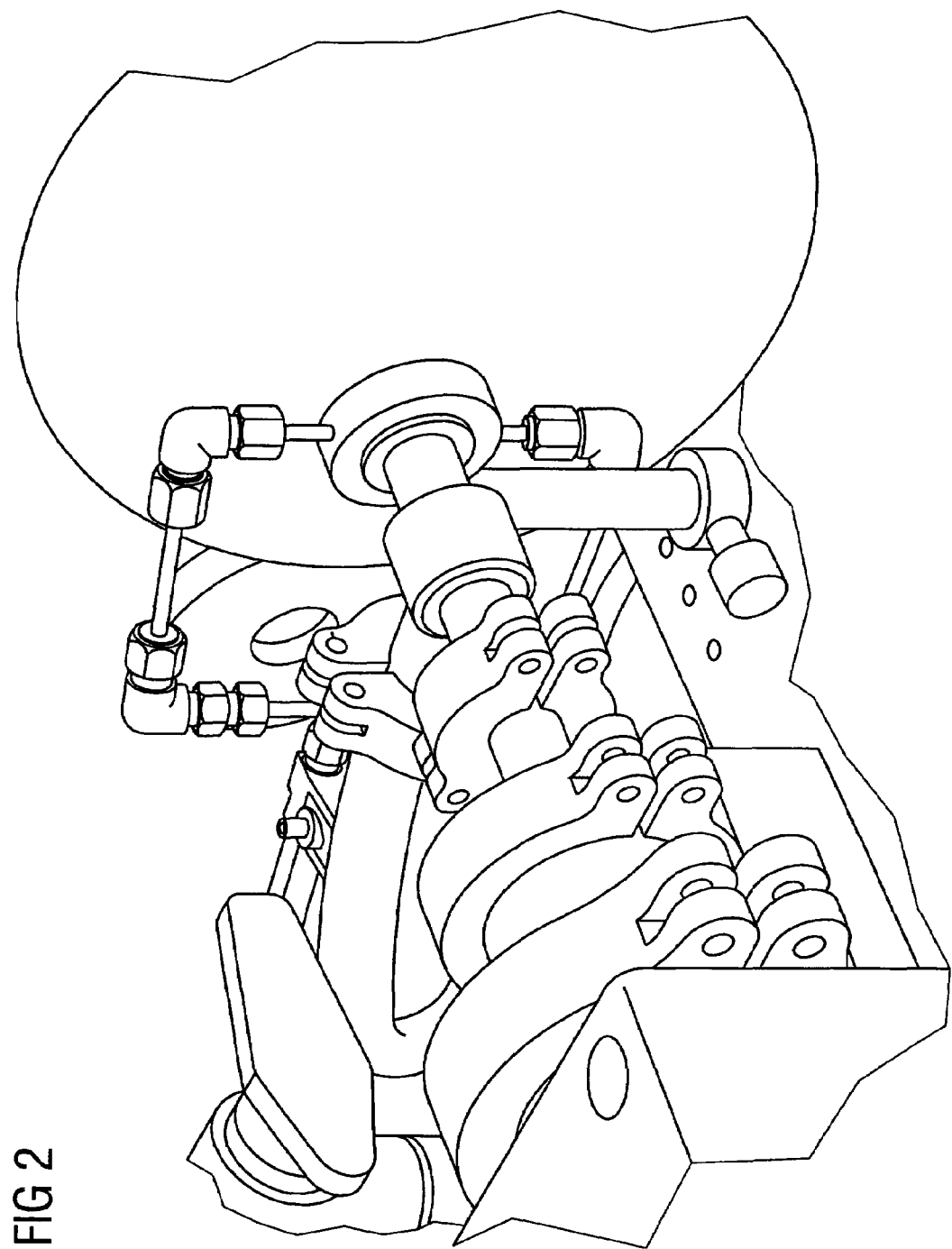
FIG. 2 shows an embodiment of the apparatus according to the invention in use.

A laser 1 emits a laser beam 8 at a wavelength of, for example, 248, 193, or 157 nm, which is suitable for exposing of the photoresist to be investigated. The laser beam 8 passes through beamforming optics 2. The laser beam 8 is focused in accordance with the exposure requirements, and/or is widened and aligned with the area to be irradiated, in these beamforming optics 2.

After the beamforming optics 2, the laser beam 8 passes through the proof plate holder 4, which can be evacuated, in which the proof plate 3 is fixed on its holder by means of a vacuum 9. The holder can be ventilated with nitrogen 10 in order to release the proof plate 3 from its holder.

The area to be irradiated is located on a substrate 5. The substrate 5 is mounted on a substrate holder 6. The substrate holder 6 is motorized, and can be rotated and moved.

A movable detector 7 for measurement of the incident radiation dose is located alongside the substrate 5.

The laser beam 8 which is emitted from the laser 1 and is focused by the beamforming optics 2 strikes the substrate 5, with exposure products being formed on the surface of the substrate 5, which outgas from the surface.

The outgassing compounds are adsorbed on a proof plate 3, and can subsequently be subject to a chemical analysis.

An annular nitrogen flow 11, which is provided around the proof plate 3, ensures an oxygen-free environmental atmosphere, and reduces concentration gradients.

While the invention has been described in detail and with reference to specific embodiments thereof, it will be apparent to one skilled in the art that various changes and modifications can be made therein without departing from the spirit and scope thereof. Accordingly, it is intended that the present invention covers the modifications and variations of this invention provided they come within the scope of the appended claims and their equivalents.

LIST OF SYMBOLS

1 Laser
2 Beamforming optics
3 Proof plate
4 Proof plate holder
5 Substrate
6 Substrate holder (motorized)
7 Detector
8 Laser beam
9 Gas outlet (vacuum)
10 Gas inlet
11 Annular nitrogen flow

We claim:

1. An apparatus for proof of outgassing products, comprising:
    a radiation source for emitting radiation;
    beamforming optics;
    a substrate holder; and
    a proof plate operable to adsorb outgassing products that are emitted from a substrate attached to a substrate holder, wherein the proof plate is fixed by the holder in immediate vicinity of and apart from the substrate, and wherein a nitrogen flow flows around the proof plate.

2. The apparatus as claimed in claim 1, further comprising: a detector for measuring the radiation.

3. The apparatus as claimed in claim 1, wherein the substrate comprises a photoresist.

4. The apparatus as claimed in claim 3, wherein the photoresist comprises a chemically enhanced photoresist.

5. The apparatus as claimed in claim 3, wherein the photoresist is applied to a wafer.

6. The apparatus as claimed in claim 1, wherein the radiation is at a wavelength less than 200 nm.

7. The apparatus as claimed in claim 1, wherein the nitrogen flows around the proof plate in an annular shape.

8. The apparatus as claimed in claim 1, wherein the proof plate is disposed 0.3 mm in front of the substrate.

9. The apparatus as claimed in claim 1, wherein the substrate holder is at least one of rotatable and movable.

10. A method for proof of outgassing products, comprising:
    providing an apparatus for outgassing products including:
        a radiation source for emitting radiation;
        beamforming optics for forming a beam from the emitted radiation;
        a substrate holder; and
        a proof plate for adsorption of the outgassing products emitted from a substrate;
    attaching the substrate to the substrate holder;
    fixing the proof plate to a proof plate holder to dispose the proof plate in immediate vicinity of and apart from the substrate;
    generating a nitrogen flow around the proof plate;
    irradiating an area on the substrate via the beam by passing the beam through the proof plate; and
    adsorbing on the proof plate outgassing products generated by the irradiation of the substrate area by the beam.

11. An apparatus for collecting outgassing products comprising:
    a radiation source;
    beamforming optics configured to focus the radiation emitted by the radiation source and align the radiation with a desired irradiation area;
    a substrate holder; and
    a proof plate disposed between the radiation source and the substrate holder, wherein the proof plate is capable of adsorbing outgassing products released by a substrate positioned on the substrate holder.

12. The apparatus of claim 11, wherein the focused radiation passes though the proof plate.

13. The apparatus of claim 11, wherein the proof plate is arranged proximate the substrate.

14. The apparatus of claim 11, wherein the proof plate is arranged a short distance in front of the substrate.

15. The apparatus of claim 11 further comprising a nitrogen source configured to direct a flow of nitrogen around the proof plate.

16. A method of collecting outgassing products comprising:
   (a) providing an apparatus including:
      a radiation source,
      beamforming optics configured to focus the radiation emitted by the radiation source and align the radiation with a desired irradiation area,
      a substrate holder, and
      a proof plate disposed between the radiation source and the substrate holder;
   (b) receiving a substrate on the substrate holder;
   (c) directing the radiation emitted by the radiation source through the beamforming optics to form a beam of radiation; and
   (d) directing the beam of radiation onto the substrate to form outgassing products,
   wherein the proof plate is positioned such that the outgassing products released by the substrate are precipitated on the proof plate via adsorption.

17. The method of claim 1, wherein the apparatus further comprises a nitrogen source and the method further comprises flowing nitrogen around the proof plate to minimize substrate contamination.

18. The method of claim 1, wherein the method further comprises (e) chemically analyzing the adsorbed outgassing precipitates.

* * * * *